United States Patent [19]

Abele

[11] Patent Number: 5,631,289

[45] Date of Patent: May 20, 1997

[54] USE OF CALCIUM FORMATE IN ORALLY ADMINISTRABLE COMPOSITIONS

[75] Inventor: Ulf Abele, Munchen, Germany

[73] Assignee: Chevita GmbH, Pfaffenhofen/Ilm, Germany

[21] Appl. No.: 377,083

[22] Filed: Jan. 26, 1995

[30] Foreign Application Priority Data

Jan. 28, 1994 [DE] Germany ............................ 44 02 544.0

[51] Int. Cl.$^6$ .................................................. A61K 31/19
[52] U.S. Cl. ............................................................ 514/557
[58] Field of Search .................................... 424/602, 682; 514/557

[56] References Cited

U.S. PATENT DOCUMENTS

| | | | |
|---|---|---|---|
| 4,599,330 | 7/1986 | Boeis et al. | 514/167 |
| 4,931,290 | 6/1990 | Rebhan | 424/692 |
| 5,393,535 | 2/1995 | Kjems | 424/678 |

*Primary Examiner*—Raymond Henley, III
*Attorney, Agent, or Firm*—Lowe, Price, LeBlanc & Becker

[57] ABSTRACT

The invention concerns the use of calcium formate in the form of orally administrable compositions for purposes of prophylaxis and metaphylaxis of calcium deficiency in animals. The object of the present invention is a calcium compound extensively precluding the partly pathological tissue irritations in the animal stomach-intestine tract while evincing adequately high calcium content in a comparatively small administered volume. The invention rests on the surprising insight that the drawbacks known in the state of the art can be averted by using calcium formate in the form of orally administrable compositions in the prophylaxis, therapy and metaphylaxis of calcium-deficiency symptoms. In particular the solution of the invention relates to using calcium formate bound into a gel or a paste.

10 Claims, No Drawings

USE OF CALCIUM FORMATE IN ORALLY ADMINISTRABLE COMPOSITIONS

The invention concerns the use of calcium formate in the manner defined in claim 1.

The use of solvents containing calcium salts in the preparation of orally administered therapy, prophylaxis and metaphylaxis of symptoms of calcium deficiency in cows, in particular regarding milk fever, is known. In particular those calcium compounds are used which are well water-soluble and are quickly resorbed from the digestive tract.

A significant proportion of all cows falls sick with milk fever immediately upon calving or with the onset of lactation (birthing paresis) which is triggered by a substantial calcium deficiencies in the animals' blood.

It is known to treat this sickness by intravenous injections of calcium, in particular in the form of calcium gluconate. Because intravenous calcium injection is costly especially with cattle, and because this disease cyclically recurs in animals once afflicted with it, it is further known to provide therapy by oral administration of dissolved calcium compounds, in particularly also of an easily resorbing calcium salt, or to administer prophylactically these easily resorbing calcium preparations.

As a rule these calcium preparations are administered to the animal in the form of a highly concentrated solution of calcium chloride, in other words, they are poured into the animals' mouths. Because the bad, namely from bitter to acutely burning taste and because of local irritations as well as mucous-membrane corrosion caused by such calcium chloride solutions, the animals reject these preparations. Moreover there is the implicit danger that such a highly burning solution shall not reach the digestive tract of the animal, but instead, because of improper swallowing, it reaches the air pipe or the lungs, and in the worst case may even cause death.

Accordingly it is impossible in a practical way to use this administration of calcium chloride solution as a general step against calcium deficiency, in particular to prevent milk fever, unless there be supervision by a veterinary.

In spite of the drawbacks of this low-viscosity calcium chloride solution, it has been used for many years. The problem of improperly swallowing the liquid into the air pipe and lungs can be substantially lessened by administering the calcium chloride solution in the form of a water-based gel and an inert cellulose derivative.

Because of the problems of ingestion present in all the above stated forms of administration wherein calcium chloride, even if bound in a gel, is being administered, because the preparations taste bitter-to-burning and hence taste bad and in part even cause corrosion of the digestive tract as far as into the rumen, a search was undertaken for a form of administration which would offer substantially improved taste and wherein the danger of corrosion and of local irritations shall be much reduced.

It is known to bind a dissolved calcium salt into a water-in-oil emulsion, a calcium salt being dissolved in the aqueous phase of this water-in-oil emulsion and the oil phase consisting of an oil suitable as feed. In this case too the well-soluble calcium component of calcium chloride was resorted to. A suitable oil may be vegetable oil, for instance sunflower oil, peanut oil and others. However animal oils such as fish oil also may be used in the oil phase. Even though this water-oil emulsion no longer is as bad-tasting and is less corrosive and gentler than a pure solution of calcium chloride heretofore administered in the case of milk fever, these water-in-oil emulsions as well may on occasion cause clinical symptoms and nevertheless cause even if only minor pathological tissue changes in the stomach-intestinal tract of the animals and elicit some resistance by the animals.

The administered single dose of previous calcium-chloride preparations is between 370 and 500 ml, the calcium content (Ca++) being about 50 g. As the least volume is desirable for administration, only calcium chloride appeared applicable as a calcium compound for such application, on one hand because of its high calcium content and on the other hand because of its excellent solubility in water.

In the light of this state of the art, it is the object of the present invention to find a calcium compound of less revolting taste and which substantially excludes partly pathological tissue irritations in the animal stomach-intestinal tract and which provides adequate content of calcium in a relatively small volume of administration.

The invention rests on the surprising insight that the above stated drawbacks can be averted by using calcium formate in orally administered compositions for prophylactic, therapeutic and metaphylactic purposes applied to calcium deficiency symptoms.

It was found by means of control tests using agents containing calcium chloride as water-in-oil emulsions that the administration of calcium formate in particular in the form of an aqueous gel is successful in the prophylaxis, metaphylaxis and especially the therapy of milk fever in cows.

The resorption of calcium from calcium formate through the digestive tract is comparably effective with the resorption from calcium chloride of heretofore known products. However, contrary to the case of calcium chloride, calcium formate causes no corrosion or irritation of the mucous membranes in the digestive tract. Because of the substantially better taste of calcium formate compared to calcium chloride, the former is much more readily accepted by the animals which struggle much less during administration and thus the work of the farmer or veterinarian is made much easier.

The binding of the calcium formate into a gel or a paste on one hand and the improved taste of the calcium preparation on the other hand offer the advantage that this preparation is well accepted by the animal and that as a result the dreaded aspiration into the respiratory tracts or the lungs by improper swallowing is excluded almost entirely.

The invention also rests on the insight that the calcium compound being used need not be a complete solution already in the product. It suffices wholly that the calcium formate be present in the form of a suspension uniformly distributed in the product and that it shall be dissolved only in the digestive tract and hence become resorbable and physiologically available. This problem is solved by the invention in that the calcium formate is dissolved only in a slight part in the product, while being present mostly as a gel or paste suspension, whereby this suspension cannot separate. In this manner it is advantageously possible to reduce the volume to be administered while the calcium-formate gel is still flowing and pourable to 300 to 350 ml and the volume to be administered in the case of a calcium-formate paste to about 200 to 250 ml, the Ca++ content in each case being about 50 g, whereby administration is made much easier yet.

Aside the calcium formate, combinations of compounds of magnesium and/or phosphorus also may be bound into the gel or paste. Moreover such gel or paste may contain taste-enhancing additives liked by animals so they accept this preparation without hesitation.

Gels into which to bind the calcium formate may be both oleo-gels and aqueous gels.

The invention is elucidated below by means of two illustrative modes of implementation.

Illustrative modes of implementation are gels with calcium formate as a supplement feed to be used in the prophylaxis and metaphylaxis of post-natal calcium deficiency (milk fever) in cows, sheep or goats.

ILLUSTRATIVE IMPLEMENTATION 1

The product Baymix® Calform to be commercially available in the future also may be used in the invention. The composition of this product is as follows:

| | |
|---|---|
| $Ca(COOH)_2$ | 38.83% |
| $MgCl_2.6H_2O$ | 00.96 |
| Water | 59.36 |
| Gel-forming agent and scents | 0.85 |

This product is an aqueous gel easily poured into the animal's mouth.

ILLUSTRATIVE IMPLEMENTATION 2

This product is an oleo-gel in the form of a paste administered using an applicator into the animal mouth. The composition of the product is as follows:

| | |
|---|---|
| $CA(COOH)_2$ | 55.40% |
| Peanut oil | 42.30 |
| Aerosil | 00.90 |
| Antioxidants | 00.10 |
| Scents | 00.30 |
| Adjuvants | 01.00 |

I claim:

1. A method for treating calcium deficiency by orally administering to an animal in need thereof a composition comprising calcium formate in a gel or paste form, said composition providing for prophylaxis and metaphylaxis of calcium deficiency in said animal.

2. The method of treating calcium deficiency as defined in claim 1, characterized in that calcium formate is administered as therapy for cattle milk-fever.

3. The method of treating calcium deficiency as defined in claim 1, characterized in that the calcium formate is bound into a gel or a paste further comprising magnesium and/or phosphorus.

4. A method for treating calcium deficiency in an animal in need thereof comprising orally administering a composition comprising calcium formate to said animal, wherein said composition is in the form of a gel or a paste.

5. The method for treating calcium deficiency in animals in need thereof as defined in claim 4, wherein the calcium formate is administered as therapy for cattle-milk fever.

6. The method for treating calcium deficiency in animals in need thereof as defined in claim 4, where said gel or paste further comprises magnesium and/or phosphorus.

7. A method of treating milk-fever in an animal in need thereof comprising orally administering a composition comprising calcium formate in the form of a gel or paste to said animal, wherein said animal is selected from the group consisting of cattle, sheep and goats.

8. The method of treating milk-fever in an animal as defined in claim 7, wherein said animal is a cattle.

9. The method of treating milk-fever in an animal as defined in claim 7, wherein said animal is a sheep.

10. The method of treating milk-fever in an animal as defined in claim 7, wherein said animal is a goat.

* * * * *